(12) United States Patent
Bell et al.

(10) Patent No.: US 8,197,798 B2
(45) Date of Patent: Jun. 12, 2012

(54) HAIR TREATMENT COMPOSITIONS

(75) Inventors: Fraser Ian Bell, Wirral (GB); Karen Maria Devine, Wirral (GB); Ezat Khoshdel, Wirral (GB); Yann Leray, Wirral (GB); Teresa Lyons, Wirral (GB); Colina MacKay, Wirral (GB); Yvonne Christine Plant, Wirral (GB); Richard Skinner, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 362 days.

(21) Appl. No.: 12/086,449

(22) PCT Filed: Dec. 7, 2006

(86) PCT No.: PCT/EP2006/011815
§ 371 (c)(1),
(2), (4) Date: Jul. 6, 2010

(87) PCT Pub. No.: WO2007/068400
PCT Pub. Date: Jun. 21, 2007

(65) Prior Publication Data
US 2010/0284952 A1 Nov. 11, 2010

(30) Foreign Application Priority Data

Dec. 16, 2005 (EP) .................................. 05257770

(51) Int. Cl.
*A61K 8/00* (2006.01)
(52) U.S. Cl. .................................... 424/70.1; 424/70.13
(58) Field of Classification Search .................. None
See application file for complete search history.

(56) References Cited

U.S. PATENT DOCUMENTS

| 4,412,943 A | 11/1983 | Hirota et al. ............... 252/546 |
| 4,592,907 A | 6/1986 | Akimoto et al. ............. 424/70 |
| 6,013,250 A | 1/2000 | Cannell et al. ............ 424/70.51 |
| 2002/0031483 A1* | 3/2002 | Beck et al. ................. 424/70.1 |
| 2002/0119174 A1* | 8/2002 | Gardlik et al. ............... 424/401 |
| 2004/0234489 A1 | 11/2004 | Muller ..................... 424/70.22 |

FOREIGN PATENT DOCUMENTS

| EP | 0 681 826 | 11/1995 |
| EP | 1 466 592 | 10/2004 |
| GB | 2 322 550 | 9/1998 |
| JP | 06 279227 | 10/1994 |
| JP | 06 287110 | 10/1994 |
| WO | 99/62462 | 12/1999 |
| WO | 00/16734 | 3/2000 |
| WO | 00/71086 | 11/2000 |
| WO | 02/15852 | 2/2002 |
| WO | 03/045340 | 6/2003 |
| WO | 2004/006874 | 1/2004 |
| WO | 2004/054525 | 7/2004 |
| WO | 2004/054526 | 7/2004 |
| WO | 2005/094761 | 10/2005 |
| WO | 2005/097048 | 10/2005 |

OTHER PUBLICATIONS

PCT International Search Report in PCT application PCT/EP2006/011811.
PCT International Search Report in PCT application PCT/EP2006/011813.
PCT International Search Report in PCT application PCT/EP2006/011815.
Co-pending Application: Applicant: Bell et al., U.S. Appl. No. 12/086,451.
Co-pending Application: Applicant: Bell et al., U.S. Appl. No. 12/086,450.
Japanese Patent Abstract JP 06-287110—published Oct. 11, 1994.
Japanese Patent Abstract JP 06-279227—published Oct. 4, 1994.
European Search Reprt in EP application 05 25 7770.
European Search Reprt in EP application 05 25 7773.
European Search Reprt in EP application 05 25 7772.

* cited by examiner

*Primary Examiner* — Robert A Wax
*Assistant Examiner* — Jessica Worsham
(74) *Attorney, Agent, or Firm* — Ronald A. Koatz

(57) ABSTRACT

The invention provides a hair treatment composition comprising a combination of a sugar, an aliphatic amino acid and a basic amino acid. The composition is particularly suitable for the treatment of hair which is dry, damaged and/or prone to manageability problems.

7 Claims, No Drawings

HAIR TREATMENT COMPOSITIONS

FIELD OF THE INVENTION

The invention relates to hair treatment compositions which comprise a combination of a sugar, an aliphatic amino acid and a basic amino acid. The compositions are particularly suitable for the treatment of hair which is dry, damaged and/or prone to manageability problems.

BACKGROUND AND PRIOR ART

Hair can suffer damage from a number of sources. For example, environmental sources of hair damage include such as exposure to UV and chlorine. Chemical sources of hair damage include treatments such as bleaching, perming and straightening, and overly frequent washing with harsh surfactant-based cleansing shampoo compositions. Mechanical sources of hair damage include excessive brushing and combing and prolonged use of heated appliances for drying and styling the hair.

Damage to the hair typically manifests itself in cuticle and protein loss from the hair fibre, hair fibre dryness, hair fibre brittleness and breakage and frayed or split ends. Dry, damaged hair is particularly prone to manageability problems, resulting in symptoms such as "flyaway" hair which is difficult to style or which does not retain a style, especially under conditions such as high humidity.

Various organic molecules and combinations thereof have been suggested for use in the treatment of dry, damaged and/or unmanageable hair.

For example, WO 2004054526 describes hair treatment compositions for the care and repair of damaged hair, and for improving hair manageability, comprising a disaccharide, (in particular trehalose), and a diacid (in particular adipic acid).

WO 2004054525 describes hair treatment compositions for the care and repair of damaged hair, and for improving hair manageability, comprising a disaccharide (in particular trehalose), and a diol (in particular 3-methyl-1,3-butanediol).

WO 2004006874 describes hair treatment compositions for repairing and preventing the principal symptoms of damaged hair, comprising specific branched amine and/or hydroxy compounds (in particular 3,3-dimethyl-1,2-butanediol).

The present inventors have found that hair treatment compositions comprising a combination of a sugar, an aliphatic amino acid and a basic amino acid show improved efficacy in the treatment of hair which is dry, damaged and/or prone to manageability problems.

SUMMARY OF THE INVENTION

The present invention provides a hair treatment composition comprising a combination of a sugar, an aliphatic amino acid and a basic amino acid.

The invention also provides the use of the above composition in the treatment of dry, damaged and/or unmanageable hair.

The invention also provides a method of treating hair by applying the above composition to the hair.

DETAILED DESCRIPTION AND PREFERRED EMBODIMENTS

Sugar

The composition of the invention comprises at least one sugar.

By 'sugar' is generally meant monosaccharides, disaccharides and lower oligosaccharides (typically containing between 3 and 6 monosaccharide units linked together by glycosidic bonds).

Monosaccharides are preferred for use in the invention. The term 'monosaccharide' (as opposed to oligosaccharide or polysaccharide) denotes a single unit, without glycosidic connection to other such units.

Monosaccharides have the molecular formula $(CH_2O)_n$, where n may be any integer from 3 to 8. Monosaccharides contain from 2 to 7 hydroxyl groups, depending on the number of carbon atoms, and either a ketone or an aldehyde group.

The monosaccharides containing an aldehyde group are conventionally called "aldoses" and the monosaccharides containing a ketone group are conventionally called "ketoses". Aldoses are preferred.

Preferred monosaccharides for use in the invention contain 4, 5, 6 or 7 carbon atoms. These are tetroses, pentoses, hexoses and heptoses, respectively.

In view of the presence of asymmetric carbons—one for the trioses (monosaccharides containing 3 carbon atoms) and several for the other monosaccharides—each monosaccharide takes the form of several stereoisomers, which can be enantiomers in the case of the trioses and enantiomers and diastereoisomers in the case of the other monosaccharides.

The pentoses and hexoses which can be used in the invention can cyclize to furanose and pyranose rings, respectively. In an aqueous medium, pentoses and hexoses will exist mainly in cyclic form.

Preferred aldoses which can be used in the invention are: erythrose and threose (which are tetroses), ribose, arabinose, xylose and lyxose, (which are pentoses), and allose, altrose, glucose, mannose, gulose, idose, galactose and talose (which are hexoses).

Preferred ketoses which can be used in the invention are: erythrulose (which is a tetrose), ribulose and xylulose (which are pentoses), and psicose, fructose, sorbose and tagatose (which are hexoses).

The ketoses can also have cyclic forms. For example, fructose can have the fructofuranose or fructopyranose form.

Mixtures of any of the above-described materials may also be used in the composition of the invention.

Preferably, the sugar used in the composition of the invention is an aldohexose, most preferably galactose.

The total amount of sugar in hair treatment compositions of the invention generally ranges from 0.01 to 10%, preferably from 0.05 to 1%, and is more preferably about 0.1% (by total weight sugar based on the total weight of the composition).

Aliphatic Amino Acid

The composition of the invention comprises at least one aliphatic amino acid.

The term "amino acid" denotes a molecule containing both an amino group and a carboxyl group. The amino acid may belong to the L- or D-series or may be racemic.

The term "aliphatic amino acid" denotes an amino acid having an aliphatic side chain.

Examples of suitable aliphatic amino acids for use in the invention have the general formula:

$$CH(COOH)(NHR^1)(R^2)$$

in which $R^1$ is hydrogen or an alkyl group having an alkyl chain length of from 1 to 20 carbon atoms, and $R^2$ is hydrogen or an alkyl group having from 1 to 4 carbon atoms.

In preferred aliphatic amino acids for use in the invention, $R^1$ is an alkyl group having from 1 to 4 carbon atoms, and $R^2$ is selected from H, $-CH_3$, $-CH(CH_3)_2$, $-CH_2CH(CH_3)_2$ and $-CH(CH_3)-CH_2CH_3$.

Mixtures of any of the above-described materials may also be used in the composition of the invention.

A most preferred material is N-methyl glycine (also known as sarcosine).

The total amount of aliphatic amino acid in hair treatment compositions of the invention generally ranges from 0.01 to 10%, preferably from 0.05 to 1%, and is more preferably about 0.1% (by total weight aliphatic amino acid based on the total weight of the composition).

Basic Amino Acid

The composition of the invention comprises at least one basic amino acid.

The term "amino acid" denotes a molecule containing both an amino group and a carboxyl group. The amino acid may belong to the L- or D-series or may be racemic.

The term "basic amino acid" denotes an amino acid which contains more basic groups (such as amino, amidino or guanidino) than carboxylic groups. Examples of such basic amino acids are natural and unnatural diamino-monocarboxylic acids, such as alpha,beta-diaminopropionic acid, alpha, gamma-diaminobutyric acid, lysine, arginine, histidine, ornithine and p-aminophenylalanine.

The basic amino acids are often isolated from natural sources in the form of salts and hydrosalts, which are also suitable for use in the invention. Such salts and hydrosalts are formed by reaction with mineral acids such as hydrochloric acid, phosphoric acid, carbonic acid, sulphuric acid, nitric acid, and the like, or the organic acids such as formic acid, acetic acid, lauric acid, chloroacetic acid and the like. A suitable example is arginine hydrochloride.

It is also possible to employ other derivatives such as N-substituted derivatives and peptide derivatives. These too may be used as salts or hydrosalts. Examples of N-substituted derivatives are N-alkanoyl derivatives and N-alkyl derivatives. Typically, in an N-alkanoyl derivative, the alkanoyl group will have an alkyl chain length of from 3 to 20 carbon atoms, preferably from 4 to 10 carbon atoms, for example N-butanoyl, N-hexanoyl and N-octanoyl. In an N-alkyl derivative, the alkyl group will typically have an alkyl chain length of from 1 to 20 carbon atoms, preferably from 1 to 4 carbon atoms, for example methyl, ethyl and n-propyl. Examples of peptide derivatives are those in which the peptide residue comprises from 2 to 8 amino acid residues or substituted amino acid residues.

Mixtures of any of the above-described materials may also be used in the composition of the invention.

Preferred basic amino acids for use in the invention are lysine, arginine, histidine, ornithine and mixtures thereof. Most preferred is arginine.

The total amount of basic amino acid in hair treatment compositions of the invention generally ranges from 0.01 to 10%, preferably from 0.05 to 1%, and is more preferably about 0.1% Thy total weight basic amino acid based on the total weight of the composition).

Product Form

Hair treatment compositions according to the invention may suitably take the form of shampoos, conditioners, sprays, mousses, gels, waxes or lotions.

Particularly preferred product forms are shampoos, post-wash conditioners (leave-in and rinse-off) and hair treatment products such as hair oils and lotions.

Shampoo Compositions

Shampoo compositions of the invention are generally aqueous, i.e. they have water or an aqueous solution or a lyotropic liquid crystalline phase as their major component.

Suitably, the shampoo composition will comprise from 50 to 98%, preferably from 60 to 90% water by weight based on the total weight of the composition.

Anionic Cleansing Surfactant

Shampoo compositions according to the invention will generally comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic cleansing surfactants are sodium lauryl sulphate, sodium lauryl ether sulphate (n)EO, (where n is from 1 to 3), sodium lauryl ether sulphosuccinate (n)EO, (where n is from 1 to 3), ammonium lauryl sulphate, ammonium lauryl ether sulphate (n)EO, (where n is from 1 to 3), sodium cocoyl isethionate and lauryl ether carboxylic acid (n)EO (where n is from 10 to 20).

Mixtures of any of the foregoing anionic cleansing surfactants may also be suitable.

The total amount of anionic cleansing surfactant in shampoo compositions of the invention generally ranges from 0.5 to 45%, preferably from 1.5 to 35%, more preferably from 5 to 20% by total weight anionic cleansing surfactant based on the total weight of the composition.

Further Ingredients

Optionally, a shampoo composition of the invention may contain further ingredients as described below to enhance performance and/or consumer acceptability.

Co-Surfactant

The composition can include co-surfactants, to help impart aesthetic, physical or cleansing properties to the composition.

An example of a co-surfactant is a nonionic surfactant, which can be included in an amount ranging from 0.5 to 8%, preferably from 2 to 5% by weight based on the total weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

RO-(G)$_n$ wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

A preferred example of a co-surfactant is an amphoteric or zwitterionic surfactant, which can be included in an amount ranging from 0.5 to about 8%, preferably from 1 to 4% by weight based on the total weight of the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The total amount of surfactant (including any co-surfactant, and/or any emulsifier) in a shampoo composition of the invention is generally from 1 to 50%, preferably from 2 to 40%, more preferably from 10 to 25% by total weight surfactant based on the total weight of the composition.

Cationic Polymers

Cationic polymers are preferred ingredients in a shampoo composition of the invention for enhancing conditioning performance.

Suitable cationic polymers may be homopolymers which are cationically substituted or may be formed from two or more types of monomers. The weight average ($M_w$) molecular weight of the polymers will generally be between 100 000 and 2 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:

cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include monomers of the formula:

A-O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14, JAGUAR C15, and JAGUAR C17.

Mixtures of any of the above cationic polymers may be used.

Cationic polymer will generally be present in a shampoo composition of the invention at levels of from 0.01 to 5%, preferably from 0.05 to 1%, more preferably from 0.08 to 0.5% by total weight of cationic polymer based on the total weight of the composition.

Suspending Agent

Preferably an aqueous shampoo composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a shampoo composition of the invention at levels of from 0.1 to 10%, preferably from 0.5 to 6%, more preferably from 0.9 to 4% by total weight of suspending agent based on the total weight of the composition.

Conditioner Compositions

Conditioner compositions will typically comprise one or more cationic conditioning surfactants which are cosmetically acceptable and suitable for topical application to the hair.

Preferably, the cationic conditioning surfactants have the formula $N^+(R^1)(R^2)(R^3)(R^4)$ wherein $R^1$, $R^2$, $R^3$ and $R^4$ are independently ($C_1$ to $C_{30}$) alkyl or benzyl.

Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl.

More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable cationic conditioning surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (e.g., Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic conditioning surfactants for use in the invention, either alone or in admixture with one or more other cationic conditioning surfactants, is a combination of (i) and (ii) below:

(i) an amidoamine corresponding to the general formula (I):

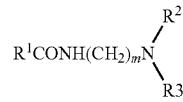

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton N.J., USA).

Acid (ii) may be any organic or mineral acid which is capable of protonating the amidoamine in the hair treatment composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, and mixtures thereof.

The primary role of the acid is to protonate the amidoamine in the hair treatment composition thus forming a tertiary amine salt (TAS) in situ in the hair treatment composition.

The TAS in effect is a non-permanent quaternary ammonium or pseudo-quaternary ammonium cationic surfactant.

Suitably, the acid is included in a sufficient amount to protonate all the amidoamine present, i.e. at a level which is at least equimolar to the amount of amidoamine present in the composition.

In conditioners of the invention, the level of cationic conditioning surfactant will generally range from 0.01 to 10%, more preferably 0.05 to 7.5%, most preferably 0.1 to 5% by total weight of cationic conditioning surfactant based on the total weight of the composition.

Conditioners of the invention will typically also incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.01 to 10%, preferably from 0.1 to 8%, more preferably from 0.2 to 7%, most preferably from 0.3 to 6% by weight of the composition. The weight ratio of cationic surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

Hair Oils and Lotions

Compositions of the invention may suitably take the form of a hair oil, for pre-wash or post-wash use. Typically, hair oils will predominantly comprise water-insoluble oily conditioning materials, such as triglycerides, mineral oil and mixtures thereof.

Compositions of the invention may also take the form of a hair lotion, typically for use in between washes. Lotions are aqueous emulsions comprising water-insoluble oily conditioning materials. Suitable surfactants can also be included in lotions to improve their stability to phase separation.

Silicone Conditioning Agents

Hair treatment compositions according to the invention, particularly water-based shampoos and hair conditioners, will preferably also contain one or more silicone conditioning agents.

Particularly preferred silicone conditioning agents are silicone emulsions such as those formed from silicones such as polydiorganosiloxanes, in particular polydimethylsiloxanes which have the CTFA designation dimethicone, polydimethyl siloxanes having hydroxyl end groups which have the CTFA designation dimethiconol, and amino-functional polydimethyl siloxanes which have the CTFA designation amodimethicone.

The emulsion droplets may typically have a Sauter mean droplet diameter ($D_{3,2}$) in the composition of the invention ranging from 0.01 to 20 micrometer, more preferably from 0.2 to 10 micrometer.

A suitable method for measuring the Sauter mean droplet diameter ($D_{3,2}$) is by laser light scattering using an instrument such as a Malvern Mastersizer.

Suitable silicone emulsions for use in compositions of the invention are available from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions/microemulsions of dimethiconol. Also suitable are amodimethicone emulsions such as DC2-8177 and DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874. In such materials, the silicone emulsion droplets are preferably formed from polydiorganosiloxanes such as those described above. One preferred form of the surface active block copolymer is according to the following formula:

$HO(CH_2CH_2O)_x(CH(CH_3)CH_2O)_y(CH_2CH_2O)_xH$ wherein the mean value of x is 4 or more and the mean value of y is 25 or more.

Another preferred form of the surface active block copolymer is according to the following formula:

$(HO(CH_2CH_2O)_a(CH(CH_3)CH_2O)_b)_2$—N—$CH_2$—$CH_2$—N$((OCH_2CH(CH_3))_b(OCH_2CH_2)_aOH)_2$ wherein the mean value of a is 2 or more and the mean value of b is 6 or more.

Mixtures of any of the above described silicone emulsions may also be used.

The above described silicone emulsions will generally be present in a composition of the invention at levels of from 0.05 to 10%, preferably 0.05 to 5%, more preferably from 0.5 to 2% by total weight of silicone based on the total weight of the composition.

Other Optional Ingredients

A composition of the invention may contain other ingredients for enhancing performance and/or consumer acceptability. Such ingredients include fragrance, dyes and pigments, pH adjusting agents, pearlescers or opacifiers, viscosity modifiers, and preservatives or antimicrobials. Each of these ingredients will be present in an amount effective to accomplish its purpose. Generally these optional ingredients are included individually at a level of up to 5% by weight of the total composition.

Mode of Use

Hair treatment compositions of the invention are primarily intended for topical application to the hair and/or scalp of a human subject, either in rinse-off or leave-on compositions, for the treatment of dry, damaged and/or unmanageable hair.

The invention will be further illustrated by the following, non-limiting Example, in which all percentages quoted are by weight based on total weight unless otherwise stated.

EXAMPLE

Formulations were prepared having ingredients as shown in the following Table 1:

TABLE 1

| Formulation ingredients | Weight % | |
|---|---|---|
| | Example 1 | Control |
| Sodium laurylether sulphate (2EO) | 12 | 12 |
| Cocoyl amidopropyldimethyl glycine | 2 | 2 |
| Silicone emulsion | 2 | 2 |
| Guar hydroxypropyl trimethylammonium chloride | 0.30 | 0.30 |
| Preservative | 0.35 | 0.35 |
| Perfume | 0.42 | 0.42 |
| Citric acid | 0.17 | 0.17 |
| Galactose | 0.1 | — |
| Sarcosine | 0.1 | — |
| Arginine | 0.1 | — |
| Water and Minors | To 100 Weight % | |

The formulation of Example 1 was compared against the control formulation across a number of performance attributes, using a rank sensory methodology.

Bleached and coloured Chinese hair switches were treated with the formulation of Example 1 and the control formulation respectively.

12 panellists were asked to assess the treated hair switches. Switches treated with the formulation of Example 1 were ranked by the panellists against switches treated with the control formulation, across the following four sensory attributes: "not squeaky during rinsing", tip alignment, style retention overnight and "hair not expanded".

Sensory data was analysed using a Friedman's two-way ANOVA for ranks.

The results (rank mean for each formulation tested) are shown in the following Table 2:

TABLE 2

| Sensory Attribute | Rank mean for Control | Rank mean for Example 1 |
|---|---|---|
| "Not squeaky during rinsing" | 5.00 | 5.40 |
| Tip alignment | 4.08 | 4.64 |
| Style retention overnight | 4.12 | 4.72 |
| "Hair not expanded" | 4.60 | 4.94 |

The sensory attribute rank direction is as follows:
"Not squeaky during rinsing": higher rank is better
Tip alignment: higher rank is better
Style retention overnight: higher rank is better
"Hair not expanded": higher rank is better The results show that, compared to the control, the formulation of Example 1 performs significantly (>90%) better on "not squeaky during rinsing" during rinsing, significantly (>95%) better on tip alignment, significantly (>95%) better on style retention overnight and significantly (>90%) better on "hair not expanded".

The invention claimed is:

1. A hair treatment composition comprising a combination of
    a) 0.1 to 10% by wt. of a monosaccharide;
    b) about 0.1 to 1% by wt. of an aliphatic amino acid having the general formula:

$CH(COOH)(NHR^1)(R^2)$ in which $R^1$ is hydrogen or an alkyl group having a chain length of from 1 to 4 carbons, and $R^2$ is selected from H, —$CH_3$, —$CH(CH_3)_2$, —$CH_2CH(CH_3)_2$ and —$CH(CH_3)CH_2CH_3$; and
    c) about 0.1 to 1% by wt. of a basic amino acid selected from the group consisting of lysine, arginine, histidine, ornithine and mixtures thereof.

2. A hair treatment composition according to claim 1, in which the monosaccharide sugar is an aldohexose.

3. A hair treatment composition according to claim 2, in which the aldohexose is galactose.

4. A hair treatment composition according to claim 1, in which the aliphatic amino acid is N-methylglycine.

5. A hair treatment composition according to claim 1, in which the basic amino acid is arginine.

6. A hair treatment composition according to claim 1, which is in the form of a shampoo, a post-wash conditioner (leave-in or rinse-off), a hair oil or a hair lotion.

7. A hair treatment composition according to claim 1, wherein the monosaccharide is galactose, the aliphatic amino acid is N-methyl glycine (sarcosine), and the basic amino acid is arginine.

* * * * *